(12) United States Patent
Anderson

(10) Patent No.: US 6,361,537 B1
(45) Date of Patent: Mar. 26, 2002

(54) SURGICAL PLATE WITH PAWL AND PROCESS FOR REPAIR OF A BROKEN BONE

(76) Inventor: Cinci M. Anderson, 2530 Vista Way, Suite F228, Oceanside, CA (US) 92054

( * ) Notice: Subject to any disclaimer, the term of this patent is extended or adjusted under 35 U.S.C. 154(b) by 0 days.

(21) Appl. No.: 09/860,406

(22) Filed: May 18, 2001

(51) Int. Cl.$^7$ ............................................. A61B 17/80
(52) U.S. Cl. ................................................... 606/69
(58) Field of Search ............................ 606/69, 70, 71, 606/60

(56) References Cited

U.S. PATENT DOCUMENTS

| | | | | |
|---|---|---|---|---|
| 1,025,008 A | * | 4/1912 | Miner .......................... | 606/71 |
| 4,763,456 A | * | 8/1988 | Giannuzzi | |
| 5,267,423 A | * | 12/1993 | Giannuzzi | |
| 5,275,601 A | * | 1/1994 | Gogolewski et al. ......... | 606/72 |
| 5,951,558 A | * | 9/1999 | Fiz .............................. | 606/70 |
| 5,997,538 A | | 12/1999 | Asnis ........................... | 606/61 |
| 6,224,602 B1 | * | 5/2001 | Hayes ......................... | 606/69 |
| 6,264,411 B1 | * | 7/2001 | DiStasio et al. ............ | 411/329 |

\* cited by examiner

Primary Examiner—Jeffrey A. Smith
(74) Attorney, Agent, or Firm—John R. Ross; John R. Ross, III

(57) ABSTRACT

A surgical plate and process for preventing screw backout of repaired bones. At least one pawl is provided on a surgical plate adjacent to a screw hole. A screw having a ratchet wheel is inserted through the hole and screwed into the bone. The pawl engages the ratchet wheel to prevent rotational movement of the screw to prevent the screw from backing out. In a preferred embodiment, a pawl plate comprising a base portion is rigidly connected to the surgical plate and a torsion bar is pivotally connected to the base portion. The pawl is positioned at the end of the torsion bar. In the preferred embodiments, several of these special screw holes with pawls, and several screws (each with a ratchet wheel) are used in bone repair.

21 Claims, 7 Drawing Sheets

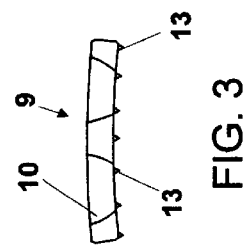
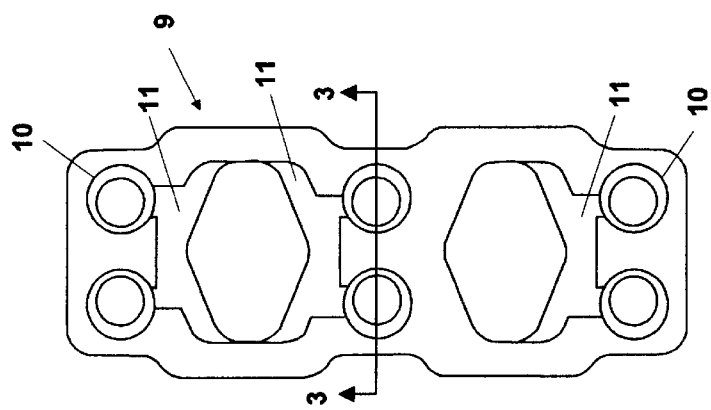
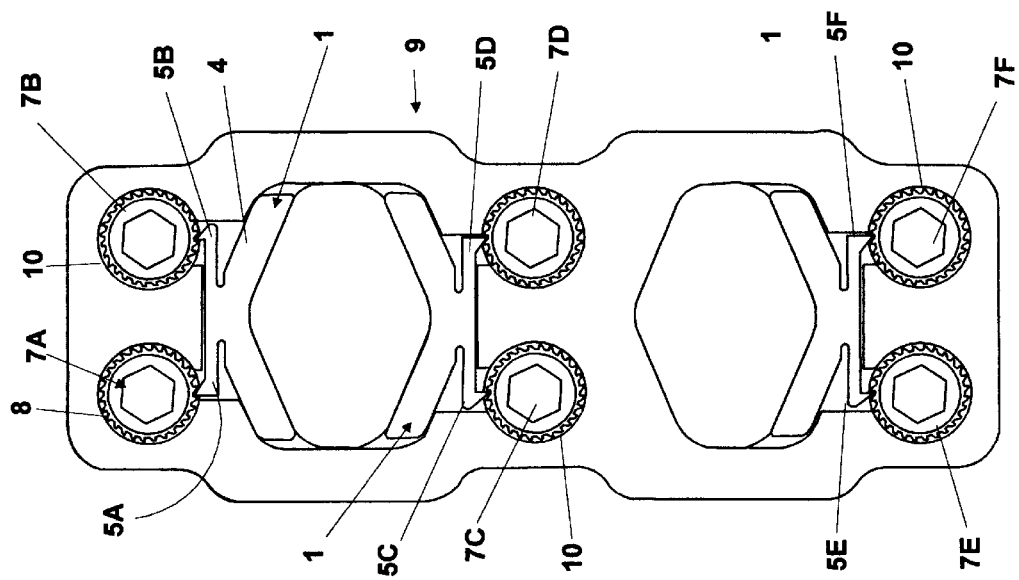

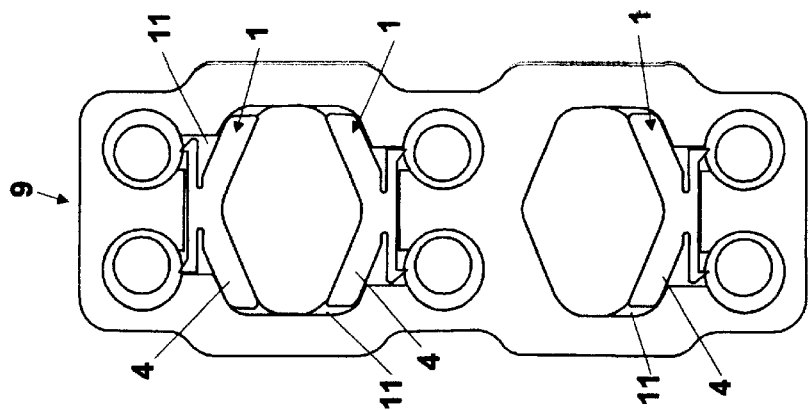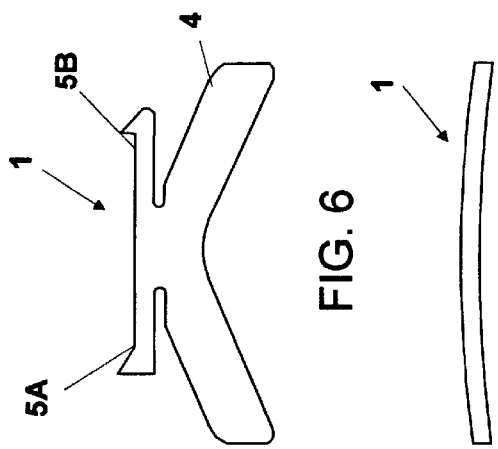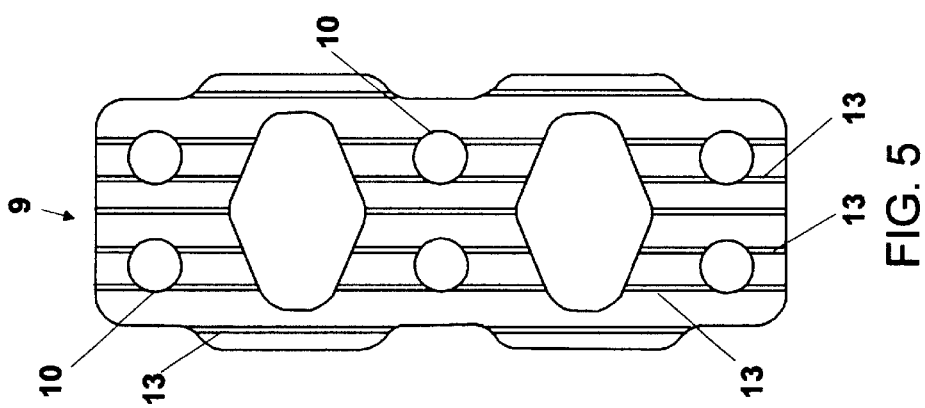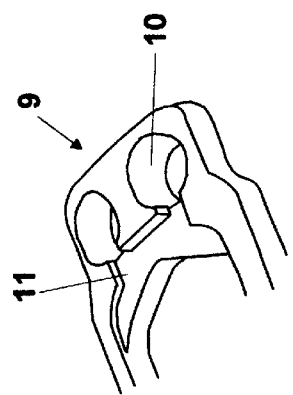

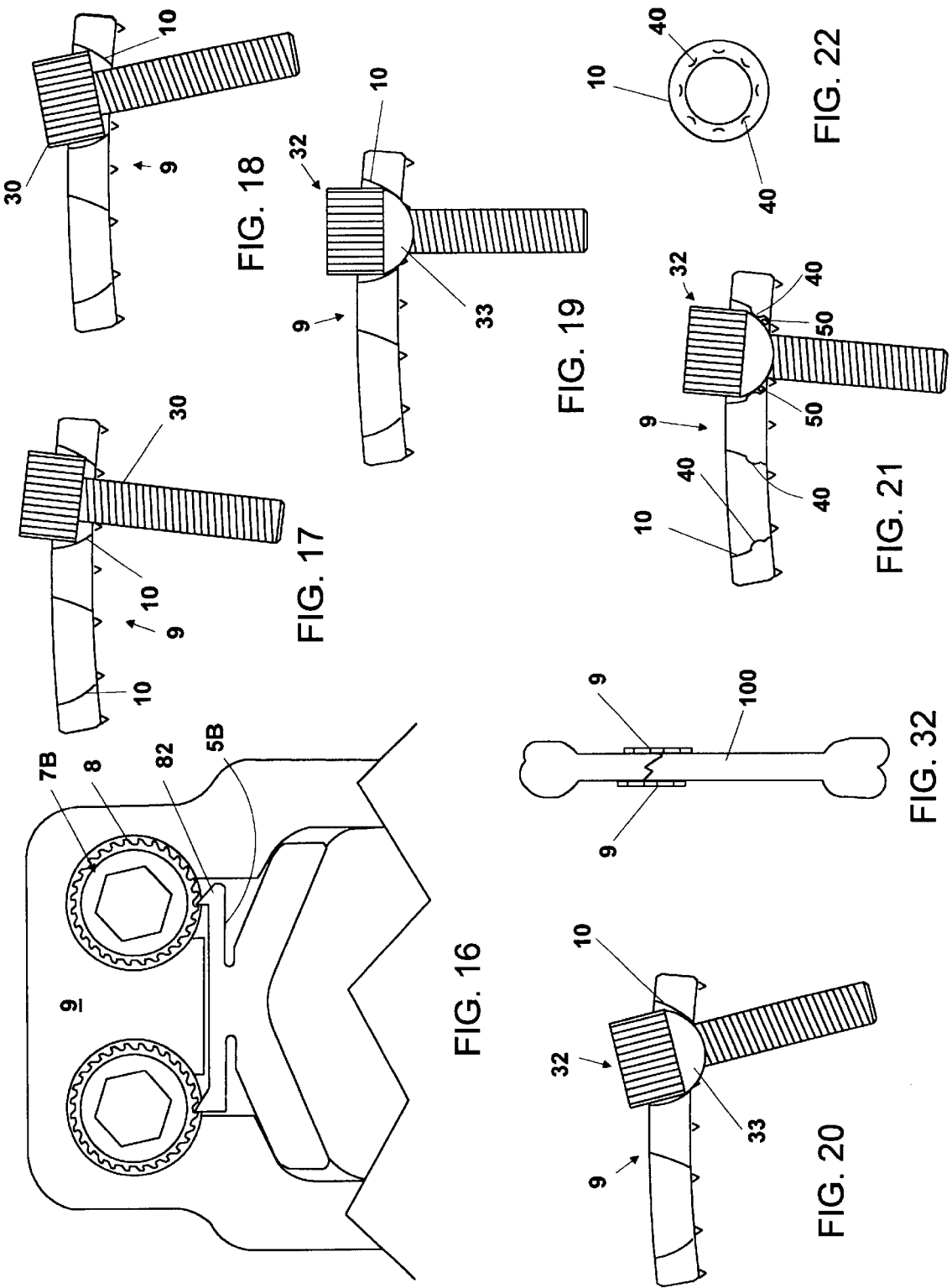

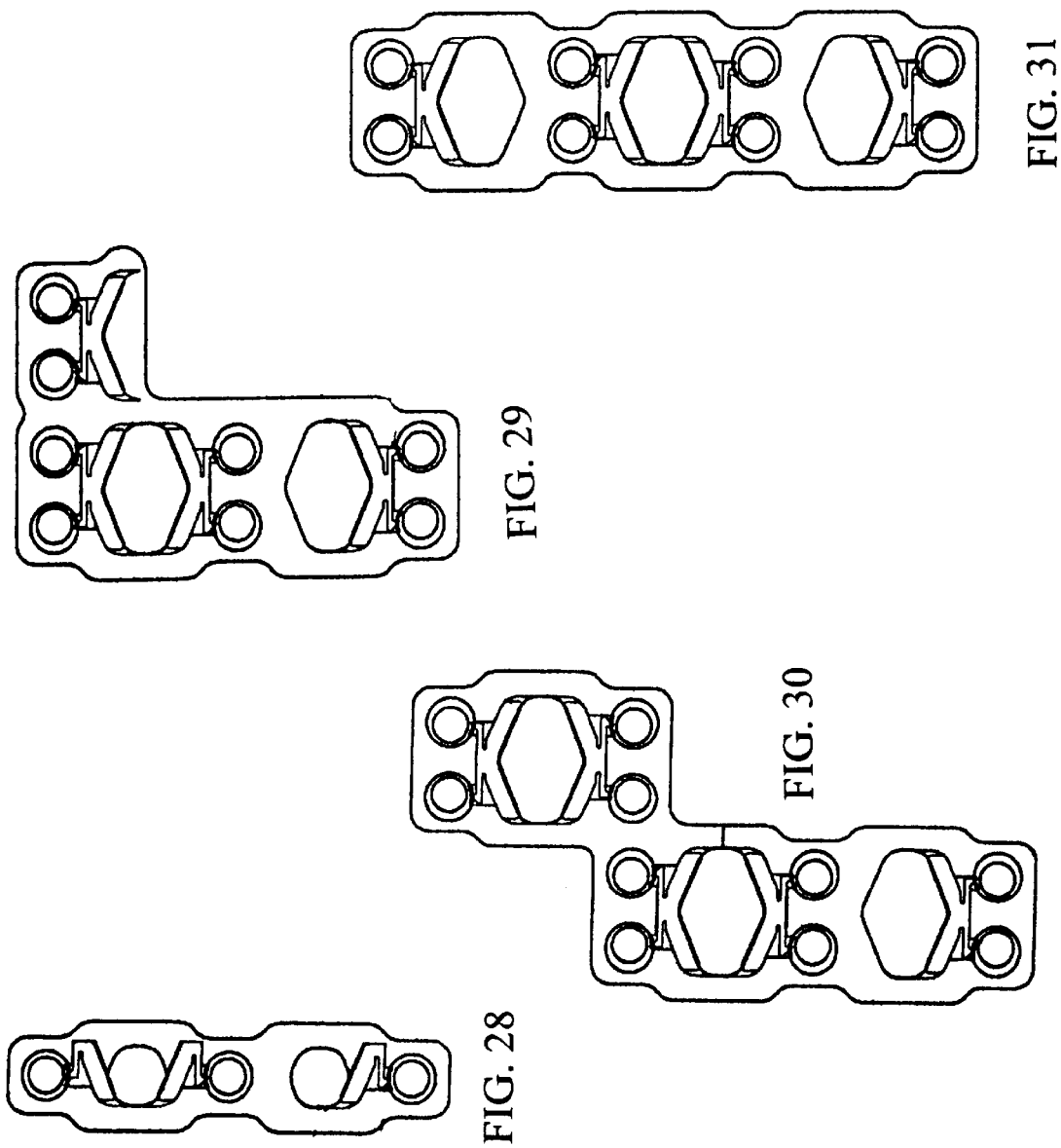

SURGICAL PLATE WITH PAWL AND PROCESS FOR REPAIR OF A BROKEN BONE

The present invention relates to surgical implants, and more specifically to surgical plates.

BACKGROUND OF THE INVENTION

Surgical plates, along with bone screws, are commonly used in the process of repairing broken bones in order to provide a distributed area of compression against the bones being clamped. Also, surgical plates are commonly used for spinal fusion or stabilization. Typically, a surgeon first places a surgical plate having screw holes onto a bone. He then drills screw holes into the bone with a drill. Then the surgeon will screw the plate onto the bone.

A problem that currently exists is that over time the screws may become loose and back out of the bone. This usually causes extreme discomfort to the patient and may lead to more serious health consequences.

What is needed is a surgical plate that is able to prevent screw backout.

SUMMARY OF THE INVENTION

The present invention provides a surgical plate and process for preventing screw backout of repaired bones. At least one pawl is provided on a surgical plate adjacent to a screw hole. A screw having a ratchet wheel is inserted through the hole and screwed into the bone. The pawl engages the ratchet wheel to prevent rotational movement of the screw to prevent the screw from backing out. In a preferred embodiment, a pawl plate comprising a base portion is rigidly connected to the surgical plate and a torsion bar is pivotally connected to the base portion. The pawl is positioned at the end of the torsion bar. In the preferred embodiments, several of these special screw holes with pawls, and several screws (each with a ratchet wheel) are used in bone repair.

BRIEF DESCRIPTION OF THE DRAWINGS

FIG. 1 shows a preferred embodiment of the present invention.

FIG. 2 shows a preferred plate.

FIG. 3 shows a cutout side view of the preferred plate of FIG. 2.

FIG. 4 shows a perspective view of a preferred plate.

FIG. 5 shows a bottom view of a preferred plate.

FIG. 6 shows a top view of a preferred pawl plate.

FIG. 7 shows a side view of a preferred pawl plate.

FIG. 8 shows a preferred plate with a pawl plate attached.

FIGS. 12–16 show the operation of a preferred embodiment of the present invention.

FIGS. 17–18 show the operation of a preferred embodiment of the present invention utilizing a preferred screw.

FIGS. 19–20 show the operation of a preferred embodiment of the present invention utilizing another preferred screw.

FIGS. 21–22 show another preferred embodiment of the present invention.

FIGS. 24–31 show other preferred embodiments of the present invention.

FIG. 32 shows a preferred embodiment of the present invention being used to repair a broken bone.

DETAILED DESCRIPTION OF THE PREFERRED EMBODIMENTS

Figure 11:
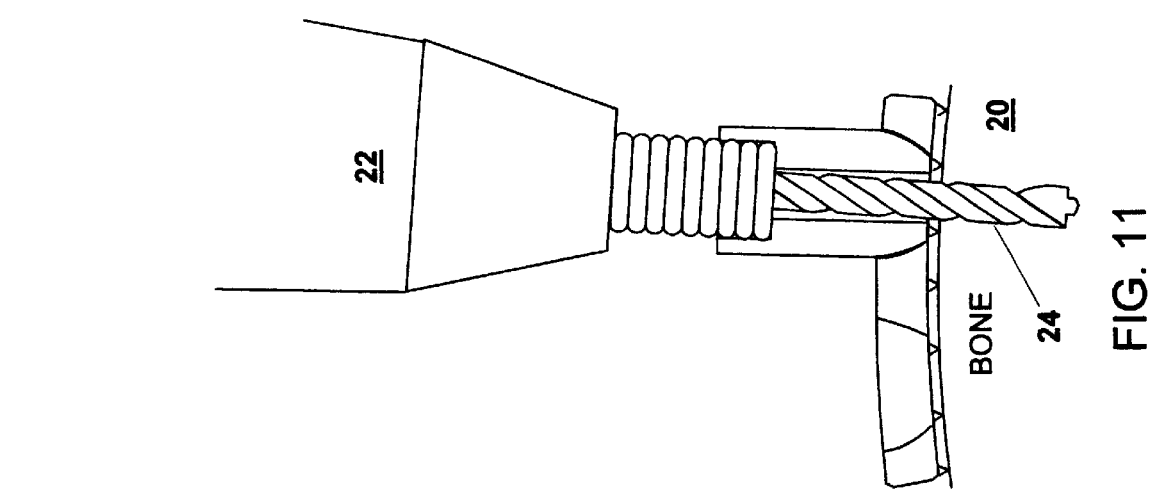
FIGS. 9–11 show a preferred method for drilling a hole into a bone.

A top view of a first preferred embodiment of the present invention is shown in FIG. 1. Bottom portion 4 of pawl plate 1 is rigidly connected to surgical plate 9. Six hex screws 7A–7F are inserted through holes 10 in surgical plate 9. Each hex screw has a ratchet wheel 8. Torsion bars 5A–5F of pawl plates 1 engage the ratchets on ratchet wheels 8 to prevent counter-clockwise rotation of hex screws 7A–7F after surgical plate 9 has been screwed into the bone of a patient.

Fabricating the First Preferred Embodiment

FIG. 2 shows a top view of surgical plate 9. FIG. 3 shows a cutout side view of surgical plate 9 and FIG. 4 shows a perspective view of surgical plate 9. FIG. 5 shows a bottom view of surgical plate 9. In the first preferred embodiment, surgical plate 9 is stainless steel and is cast by sintered powder metallurgy. As shown in FIG. 2, surgical plate 9 is approximately 1.8 inches long and approximately 0.7 inches at its widest point. As shown in FIG. 3, surgical plate 9 is slightly curved and is approximately 0.1 inch thick. As shown in FIG. 1 and FIG. 4, surgical plate 9 has three recesses 11 cut into the top of the plate. Recesses 11 are preferably approximately 0.02 inches deep.

Six holes 10 are drilled through surgical plate 9. Preferable, holes 10 are wider at the top of surgical plate 9 than they are at the bottom. In the preferred embodiment hole 10 is approximately 0.2 inches in diameter across the top of surgical plate 9 and approximately 0.14 inches in diameter across the bottom of surgical plate 9. Preferably, the walls of hole 10 are slightly curved, as shown in FIG. 3.

As shown in FIGS. 3 and 5, the bottom of surgical plate 9 preferably has seven "V" shaped compression ridges 13. When surgical plate 9 is screwed onto a bone, compression ridges 13 are able penetrate soft tissue that may be covering the bone and grip solid bone underneath the soft tissue.

FIG. 6 shows a top view and FIG. 7 shows a side view of pawl plate 1. Pawl plate 1 has bottom portion 4 and torsion bars 5A and 5B. A preferred pawl plate 1 is approximately 0.02 inches thick. As shown in FIG. 7, pawl plate 1 is slightly curved so that it fits appropriately into recess 11 (FIG. 4).

As shown in FIG. 8, each pawl plate 1 is fitted into each recess 11. Bottom portions 4 are then rigidly bond to surgical plate 9. In the preferred embodiment, bottom portions 4 are brazed to surgical plate 9.

Utilization of the First Preferred Embodiment
Drilling the Holes

Figure 10:
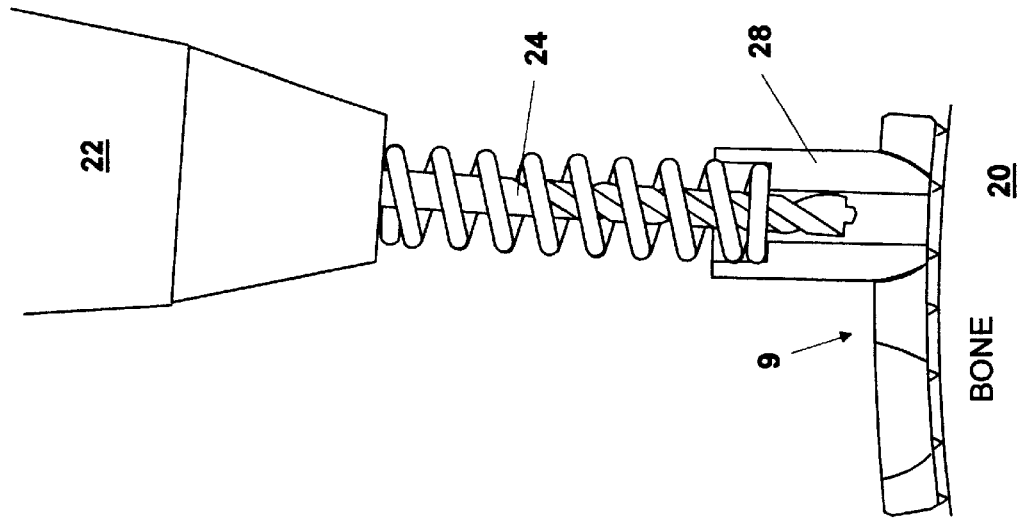
Figure 9:
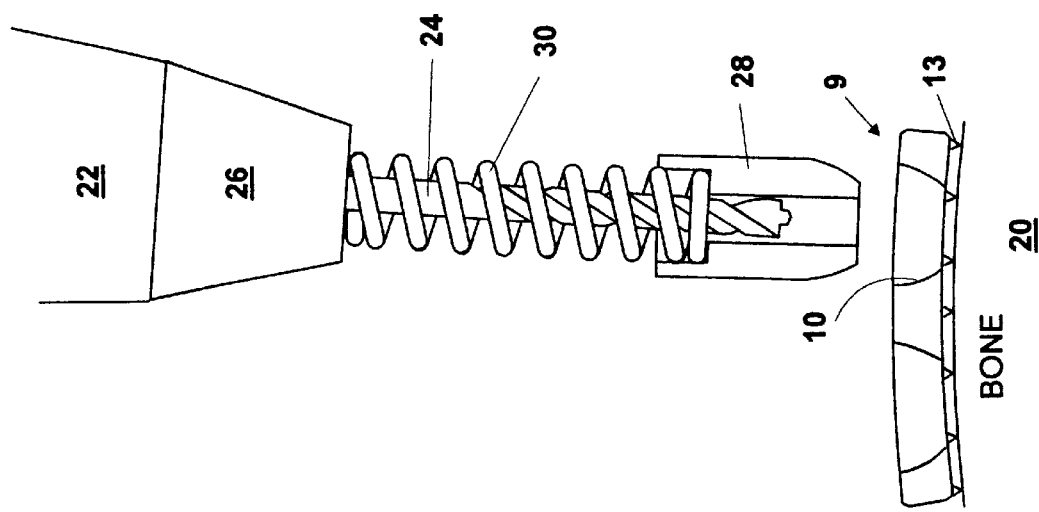

FIGS. 9–10 illustrate a preferred method for drilling holes into the bone. FIG. 9 shows a cutout side view of surgical plate 9 positioned on top of bone 20. Note that the curvature of plate 9 conforms to the curvature of bone 20. Also "V" shaped compression ridges 13 assist in the gripping of bone 20.

In the preferred embodiment, drill bushing 28 is connected to spring 30. Spring 30 is connected to drill chuck 26, which is connected to drill 22. Drill bit 24 is inserted inside and rigidly held by drill chuck 26 and extends through spring 30.

As shown in FIG. 9, drill bushing 28 is positioned over hole 10 of surgical plate 9. As shown in FIG. 10, drill bushing 28 is lowered so that it mates with hole 10 of surgical plate 9. Drill bushing 28 aligns drill bit 24 so that it is properly directed through the center of hole 10 and into bone 20.

As shown in FIG. 11, drill bit 24 is pressed downward and into bone 20. As the hole is drilled, spring force from spring 30 helps keep bushing 28 properly positioned in hole 10 and keeps the axis of the drilled hole centered.

Securing the Plate onto the Bone

Figure 12:
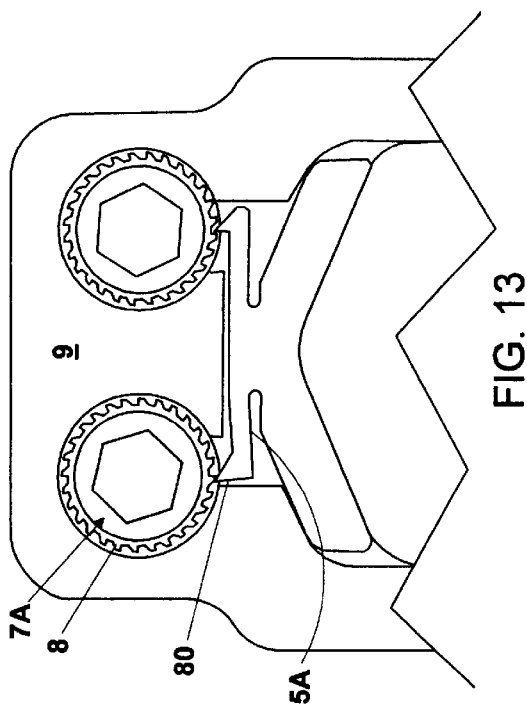

After the holes have been drilled into the bone, surgical plate 9 is securely fastened to the bone via screws 7A–7F. FIGS. 12–16 illustrate how pawl plate 1 prevents screws 7A and 7B from backing out after they have been screwed into the holes in the bone. In FIG. 12, torsion bar 5A is engaged with ratchet wheel 8 of screw 7A so as to prevent counterclockwise rotation of screw 7A and torsion bar 5B is engaged with ratchet wheel 8 of screw 7B so as to prevent counterclockwise rotation of screw 7B.

Figure 13:
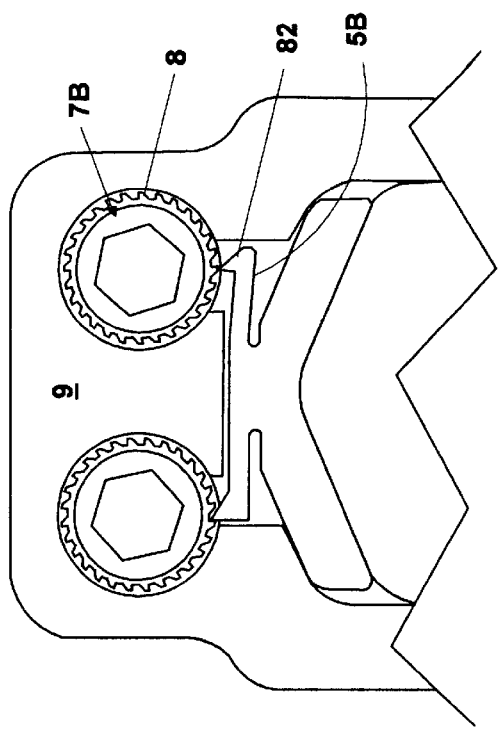

In FIG. 13, screw 7A has been turned clockwise ½ of a notch so that pawl 80 of torsion bar 5A has been moved downward as it has ridden along a ratchet of ratchet wheel 8.

Figure 14:
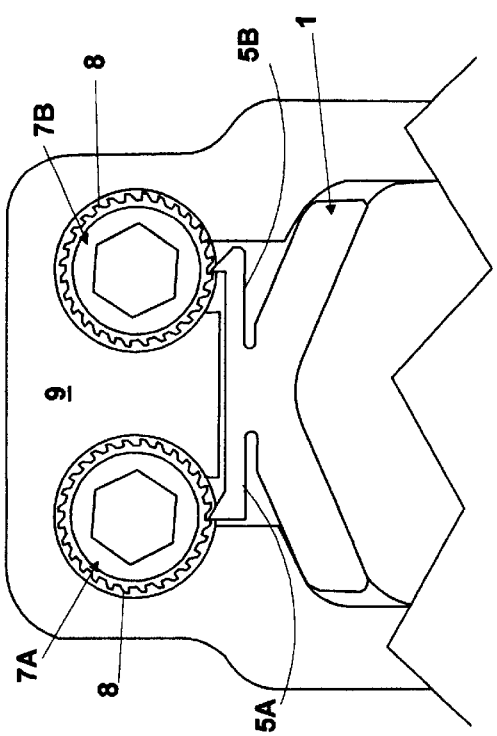

In FIG. 14, screw 7A has been turned clockwise another ½ of a notch so that torsion bar 5A has snapped back upward and is in a position to prevent counterclockwise rotation of screw 7A. In this manner, screw 7A is continually tightened until it is tightly pressing plate 9 against the bone. Screw 7A is prevented from backing out through unwanted counterclockwise rotation by pawl 80 of torsion bar 5A engaging ratchet wheel 8 of screw 7A.

Figure 15:
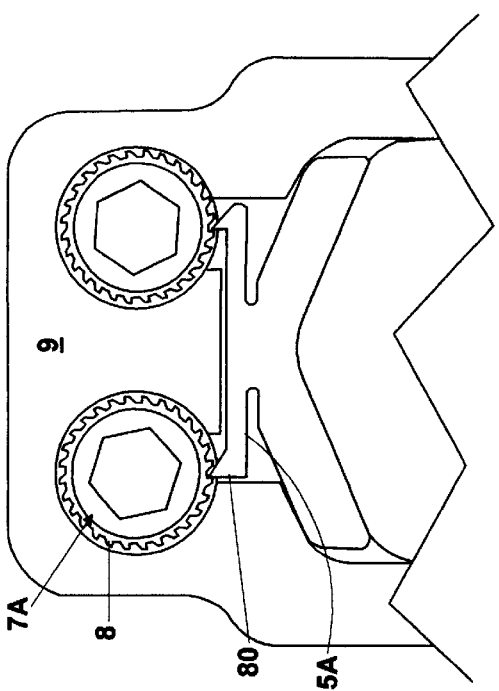
Figure 24:
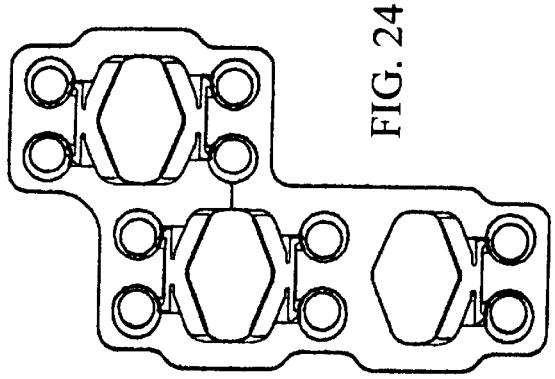
Figure 27:
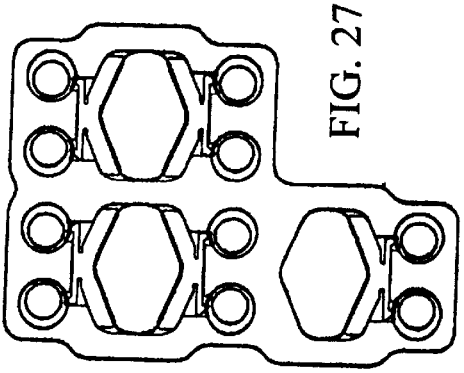

In FIG. 15, screw 7B has been turned clockwise ½ of a notch so that pawl 82 of torsion bar 5B has been moved downward as it has ridden along a ratchet of ratchet wheel 8.

In FIG. 16, screw 7B has been turned clockwise another ½ of a notch so that torsion bar 5B has snapped back upward and is in a position to prevent counterclockwise rotation of screw 7B. In this manner, screw 7B is continually tightened until it is tightly pressing plate 9 against the bone. Screw 7B is prevented from backing out through unwanted counterclockwise rotation by pawl 82 of torsion bar 5B engaging ratchet wheel 8 of screw 7B.

In a similar fashion, screws 7C–7D (FIG. 1) are all tightened. As described above, all screws are prevented from accidental unwanted backout by pawl plates 1.

However, it may be desirable to eventually purposely remove a screw after it has been tightly secured against surgical plate 9. For example, to intentionally unscrew screw 7A, a surgeon would move pawl 80 of torsion bar 5A downward to a position shown in FIG. 13 with a scalpel (or other sharp instrument). The surgeon could then merely turn the screw counterclockwise to back it out.

FIG. 32 shows a side view of two surgical plates 9 screwed into broken bone 100.

Screw Types

FIGS. 17 and 18 illustrate the utilization of conventional ratchet screws with the present invention. It should be noted that holes 10 of plate 9 allow for screw 30 to be inserted through plate 9 in a variety of angles. In this manner, the surgeon can screw conventional ratchet screw 30 into the bone at the optimum angle.

FIGS. 19 and 20 illustrate another preferred embodiment in which ratchet screw 32 has bottom hemisphere portion 33. As with conventional ratchet screw 30 shown in FIGS. 17 and 18, ratchet screw 32 can be inserted through plate 9 in a variety of angles. However, hemisphere portion 33 of ratchet screw 32 enables it to also achieve a more secure fit against the curved walls of hole 10.

Holes with Dimpled Walls

FIG. 21 shows a side view and FIG. 22 shows a top view of a preferred embodiment of the present invention in which holes 10 have dimples 40 protruding from their walls. In this preferred embodiment, screw 32 is seated against dimples 40 when tightened down. By seating against dimples 40, unwanted debris 50 (such as skin tissue or bone chips) will not accidentally get squeezed between screw 32 and the surgical plate.

Figure 23:
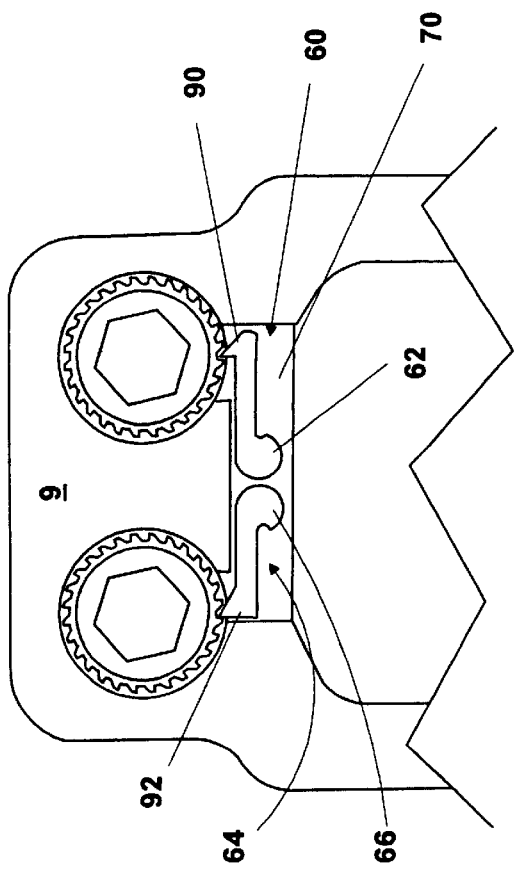
FIG. 23 shows another preferred embodiment of the present invention.
Figure 26:
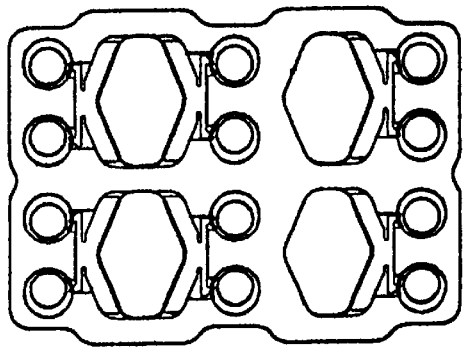
Figure 25:
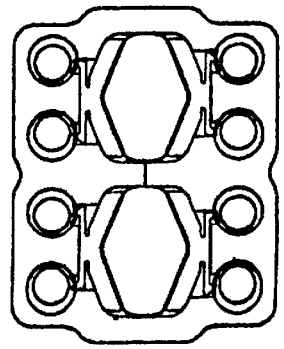

While the above description contains many specifications, the reader should not construe these as limitations on the scope of the invention, but merely as exemplifications of preferred embodiments thereof. Those skilled in the art will envision that many other possible variations are within its scope. For example, although approximate measurements were given for the first preferred embodiment, the size of the plate could be easily modified to accommodate various bone sizes. Also, although FIG. 3 shows that surgical plate 9 is only slightly curved, the degree of curvature could be increased to have a plate that is more curved or eliminated to have a flat plate. Also, although it was stated that pawl plate 1 was brazed to surgical plate 9, pawl plate 1 could be rigidly attached to surgical plate 9 utilizing other known methods, such as welding. Also, although it was stated that surgical plate 9 was cast from of stainless steel, surgical plate 9 could be made from other materials, such as titanium. Also, although FIG. 1 shows surgical plate 9 having a specific shape, it would be easy to modify the shape of the plate. For example FIGS. 24–31 show surgical plates having a variety of shapes. Also, although pawl plate 1 was shown in discussed in the above preferred embodiments, it would also be possible to torsionally connect a pawl directly to the surgical plate. For example, as shown in FIG. 23, pawl 90 is connected to torsion bar 60, which has been welded to recess 70 of surgical plate 9 at its base 62. Likewise, pawl 92 is connected to torsion bar 64, which has been welded to recess 70 of surgical plate 9 at its base 66. Also, the present invention can not only be used for human bone repair, but it can also be used for bone repair for animals. Also, in addition to the repair of a broken bone, the present invention may be used for the repair of a fractured bone, unstable vertebra and for spinal fusion. Accordingly the reader is requested to determine the scope of the invention by the appended claims and their legal equivalents, and not by the examples which have been given.

I claim:

1. A bone repair device for preventing screw backout of a repaired bone, said device comprising:

A) a surgical plate defining at least one hole,
   B) at least one pawl connected to said surgical plate and positioned adjacent to said at least one hole,
   C) at least one screw inserted through said at least one hole and for being screwed into said repaired bone, wherein said at least one screw comprises a ratchet wheel,
      wherein said at least one pawl engages said ratchet wheel to prevent rotational movement of said at least one screw to prevent said at least one screw from backing out of said bone.

2. The bone repair device as in claim 1, wherein said at least one screw is a right hand screw and said pawl prevents rotational movement of said at least one screw in the counterclockwise direction.

3. The bone repair device as in claim 1, wherein said at least one screw is a left hand screw and said pawl prevents rotational movement of said at least one screw in the clockwise direction.

4. The bone repair device as in claim 1, wherein said at least one hole is a plurality of holes, wherein said at least one pawl is a plurality of pawls, wherein said at least one screw is a plurality of screws.

5. The bone repair device as in claim 1, further comprising a pawl plate, wherein said pawl plate comprises:
   A) a base portion rigidly connected to said surgical plate, and
   B) at least one torsion bar connected to said base portion, wherein said at least one pawl is connected to said at least one torsion bar.

6. The bone repair device as in claim 1, wherein said at least one screw is a hex screw.

7. The bone repair device as in claim 1, wherein said at least one screw comprises a bottom hemisphere portion.

8. The bone repair device as in claim 1, wherein the wall of said at least one hole comprises a plurality of dimples.

9. The bone repair device as in claim 1, further comprising a plurality of "V" shaped compression ridges.

10. The bone repair device as in claim 1, wherein said at least one screw is for being screwed into at least one bone hole, wherein said at least one bone hole is drilled utilizing a drill comprising:
    A) a drill bushing defining a drill bushing hole aligned with said at least one hole of said surgical plate,
    B) a drill bit inserted through said drill bushing hole,
    C) a drill chuck for holding said drill bit, and
    D) a spring positioned between said drill bushing and said drill chuck.

11. A bone repair device for preventing screw backout, comprising:
    A) a surgical plate means defining at least one hole,
    B) at least one pawl means connected to said surgical plate means and positioned adjacent to said at least one hole,
    C) at least one screw means inserted through said at least one hole, wherein said at least one screw means comprises a ratchet wheel,
       wherein said at least one pawl means engages said ratchet wheel to prevent rotational movement of said at least one screw means to prevent said at least one screw means from backing out.

12. The bone repair device as in claim 11, wherein said at least one screw means is a right hand screw and said pawl means prevents rotational movement of said at least one screw means in the counterclockwise direction.

13. The bone repair device as in claim 11, wherein said at least one screw means is a left hand screw and said pawl means prevents rotational movement of said at least one screw means in the clockwise direction.

14. The bone repair device as in claim 11, wherein said at least one hole is a plurality of holes, wherein said at least one pawl means is a plurality of pawls, wherein said at least one screw means is a plurality of screws.

15. The bone repair device as in claim 11, further comprising a pawl plate means, wherein said pawl plate means comprises:
    A) a base portion means rigidly connected to said surgical plate means, and
    B) at least one torsion bar means connected to said base portion means, wherein said at least one pawl means is connected to said at least one torsion bar means.

16. The bone repair device as in claim 11, wherein said at least one screw means is a hex screw.

17. The bone repair device as in claim 11, wherein said at least one screw means comprises a bottom hemisphere portion.

18. The bone repair device as in claim 11, wherein the wall of said at least one hole comprises a plurality of dimples.

19. The bone repair device as in claim 11, further comprising a plurality of "V" shaped compression ridges.

20. The bone repair device as in claim 11, wherein said at least one screw means is for being screwed into at least one bone hole, wherein said at least one bone hole is drilled utilizing a drill comprising:
    A) a drill bushing means defining a drill bushing hole aligned with said at least one hole of said surgical plate means,
    B) a drill bit means inserted through said drill bushing hole,
    C) a drill chuck means for holding said drill bit means, and
    D) a spring means positioned between said drill bushing means and said drill chuck means.

21. A process for repair of a broken bone defining two parts of said bone, comprising the steps of:
    A) joining at least two parts of a broken bone together,
    B) positioning a surgical plate to cover said at least two parts of said broken bone, said surgical plate having a plurality of holes, each of said plurality of holes having a pawl positioned adjacent to it, and
    C) inserting a screw having a ratchet head into each of said plurality of holes and screwing each of said screw into said bone so that said pawl connects with said ratchet head to prevent said screw from backing out of said bone.

* * * * *